United States Patent [19]

Bokros

[11] 4,272,854
[45] Jun. 16, 1981

[54] BI-LEAFLET HEART VALVE

[75] Inventor: Jack C. Bokros, Alpine, Calif.

[73] Assignee: Carbomedics, Inc., Austin, Tex.

[21] Appl. No.: 64,400

[22] Filed: Aug. 7, 1979

[51] Int. Cl.³ ............................................. A61F 1/22
[52] U.S. Cl. ................................... 3/1.5; 137/512.1; 137/527.8
[58] Field of Search ................... 3/1.5, 1; 137/512.1, 137/527, 527.8

[56] References Cited

U.S. PATENT DOCUMENTS

| 4,011,601 | 3/1977 | Clune et al. | 3/1.5 |
| 4,159,543 | 7/1979 | Carpentier | 3/1.5 |

FOREIGN PATENT DOCUMENTS

| 2846299 | 5/1979 | Fed. Rep. of Germany | 3/1.5 |
| 1160008 | 7/1969 | United Kingdom | 3/1.5 |

Primary Examiner—Ronald L. Frinks
Attorney, Agent, or Firm—Fitch, Even, Tabin, Flannery & Welsh

[57] ABSTRACT

A heart valve prosthesis having an annular valve body defining a central passageway which is closed by a pair of pivoting leaflets. Projections extending laterally from each of the leaflets are received in socket means provided at generally diametrically opposite locations in the interior wall of the valve body. Slot portions of the socket means guide the pivotal movement of the leaflets. The pivotal axis of each leaflet is eccentrically located and moves relative to the valve body during opening and closing motion.

6 Claims, 6 Drawing Figures

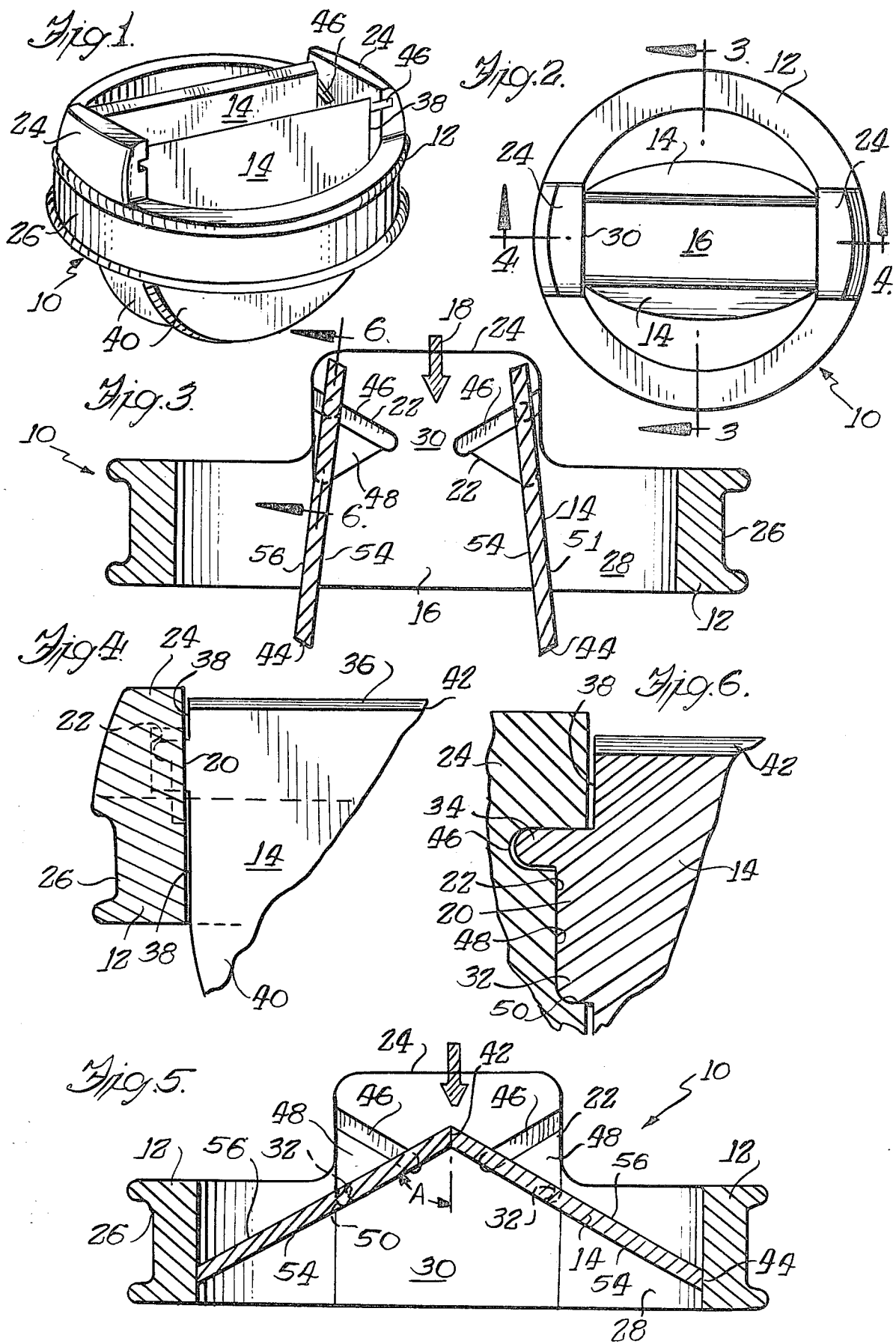

BI-LEAFLET HEART VALVE

BACKGROUND OF THE INVENTION

This invention relates to heart valves for replacement of defective natural valves and more particularly to heart valve prostheses that use a pair of pivoting valve members.

Heart valve prostheses are essentially check valves that operate hemodynamically as a result of the pumping action of the heart. An early valve of this type used a ball-and-cage arrangement; however, later valve designs have used a disc for the valve member, e.g., U.S. Pat. No. 3,534,411. Pivoting disc-type valves are shown in my U.S. Pat. Nos. 3,546,711 and in 3,859,668.

Heart valves have also been designed which use two members or leaflets instead of one disc, and such leaflets may rotate about parallel axes as a part of opening and closing of the valve. An early version of such a bi-leaflet valve is shown in British Pat. No. 1,160,008, and U.S. Pat. No. 4,078,268 also shows a valve of this type. Another such two-leaflet heart valve is shown in my U.S. Application, Ser. No. 894,166, filed Apr. 6, 1978, now U.S. Pat. No. 4,178,639.

SUMMARY OF THE INVENTION

The invention provides an improved version of a two-leaflet heart valve prosthesis. Each of the leaflets has a pair of projections that extend from its opposite sides and that are received in slots or grooves formed in diametrically opposite portions of an annular valve body. The slots are oriented at an angle from the centerline through the valve passageway and control the pivoting movement of the leaflets. The leaflets movement is also controlled by other support points also provided on the projections, and the orientation of the slots is such that, when the leaflet pivots between open and closed positions, the pivot axis of the leaflet changes.

IN THE DRAWINGS

FIG. 1 is a perspective view of a heart valve embodying various features of the invention and having a pair of leaflets which are shown in the open position;

FIG. 2 is a plan view of the valve of FIG. 1;

FIG. 3 is an enlarged sectional view taken generally along the line 3—3 of FIG. 2;

FIG. 4 is an enlarged fragmentary sectional view taken generally along the line 4—4 of FIG. 2;

FIG. 5 is a sectional view similar to FIG. 3 which shows the leaflets in closed position; and FIG. 6 is an enlarged fragmentary sectional view, taken generally along line 6—6 of FIG. 3, showing the projection of one leaflet.

DETAILED DESCRIPTION OF THE PREFERRED EMBODIMENT

FIG. 1 illustrates a heart valve 10 having an annular valve body 12 and two pivoting leaflets or valve members 14 which open and close to control the flow of blood through a central passageway 16 in the direction of arrow 18 (FIG. 3). The leaflets 14 are supported by projections 20 which are received in generally diametrically opposed sockets 22 formed in upstanding sections 24 of the annular valve body 12 which serve as standards.

The valve 10 can operate in any orientation and is not significantly affected by gravity; however, for ease of explanation, the valve 10 is shown and described with the annular valve body 12 disposed horizontal. The valve body 12 is formed with a peripheral groove 26 about its exterior surface adapted to accommodate a suturing ring, as well-known in the art, which facilitates the sewing or suturing of the heart valve 10 to the heart tissue.

The central passageway 16 through the valve body 12 is defined by an interior wall 28 and is generally circular in cross section except for the regions adjacent and below the standards 24 where flat or planar sections 30 are formed in the interior wall 28, which also define the inward-facing surfaces of the standards. Thus, the passageway 16 deviates slightly from being perfectly circular in cross section because of the diametrically opposite flat sections 30.

The valve body 12 and the leaflets 14 are made of suitable material that is biocompatible and nonthrombogenic and that will resist the wear of the countless openings and closings. The components are preferably made from isotropic polycrystalline graphite, such as that sold under the tradename POCO, which has been coated with PYROLITE pyrolytic carbon to give it excellent compatibility and wear-resistance.

The leaflets 14 are generally flat, as best seen in FIGS. 3 and 5, and can thus be formed from a piece of isotropic graphite having a uniform thickness. The pivotal axis for each of the leaflets 14 is eccentric to the leaflet and is defined by the projections 20 which extend in opposite directions from the lateral edges of the leaflets. However, as pointed out hereinafter, the design of the projections 20 and the sockets 22 is such that the pivotal axis changes during the movement of the leaflets from the fully opened position to the fully closed position. As best seen in FIG. 6, each of the projections 20 includes a lower ear or shoulder 32 which is surmounted by an upper knob section 34 that extends further laterally outward. The knob section 34 preferably has the shape of a right circular cylinder the end of which is rounded or spherical. The ear section 32 is also formed with a suitable radius of curvature throughout its entire length and including the corner portion thereof.

The upper or upstream (with respect to the flow of blood) edges 36 of the leaflets 14 are straight, and the periphery of the leaflets includes a pair of flanking sections 38 which are also straight and are perpendicular to the upstream edge 36. It is from these flanking sections 38 that the projections 20 extend. The remainder of the periphery is a curved edge 40 which is generally elliptical in shape, being defined by the intersection of the plane of the leaflet 14 with the right circular cylindrical surface 28 that constitutes the interior wall of the annular valve body.

As best seen in FIG. 5, the leaflets 14 are oriented at an angle A to the centerline of the passageway, which is between about 55° and 75°. The upstream straight edges 36 of the leaflets 14 are also machined at the same angle (relative to the upper surface) to provide edge surfaces 42 that lie flush against each other in the closed position. Likewise, the elliptical edge 40 of each of the leaflets 14 is machined so as to terminate in an edge surface 44 which is a section of the surface of a right circular cylinder having a diameter just slightly less than the diameter of the central passageway 16. The edge surface 44 fits closely along the interior wall 28 when the leaflets 14 are in the closed position.

The upstanding standards 24 each contain two sockets 22 formed in the otherwise flat surface region 30, as best seen in FIG. 3, wherein the projection portions of the leaflets are mounted for pivotal movement. Each of the sockets 22 includes a deep slotted section 46 and a shallow section 48 which underlies the slotted section 46 and tapers to a rounded base 50 having a radius of curvature just slightly larger than that of the bottom of the ear section 32 of the projection. The base 50 is oriented transverse to the centerline of the passageway as best seen in FIG. 6. The slotted section 46 is preferably curved or rounded at its interior end and may be left open at its outer end to facilitate installing the leaflets 14 in the valve body 12. The material from which the valve body 12 is made should have sufficient resiliency to allow the leaflets 14 to be snapped into position with the projections 20 received in the sockets 22; however, the open ended slots 46 facilitate this installation. As best seen in FIG. 6, the depth of each slot 46 is sufficient to accommodate the knob portion 34 of the projections 20 and the depth of the shallow, underlying section 48 of each socket is sufficient to accommodate the ear 32.

The slots 46 are carefully oriented at an angle of between 20° and about 40° to a horizontal plane (i.e., perpendicular to the centerline of the passageway), in a direction outward and upstream so as to precisely guide the leaflets 14 in their pivoting movement between the opened and closed positions. Preferably, however, the orientation of each slot 46 is such to change the pivotal axis of the leaflet and thereby guard against wear in these regions. As clearly shown in FIGS. 3 and 6, when the leaflets 14 are in the open position, the bottom of the ear 32 rests on the base 50 of the socket, and the knob 34, although constrained within the slot 46, lies slightly above the lower surface of the slot. Also, the outward edges of the shallow portions 48 of the sockets serve as stops to limit the opening movement of the leaflets. Furthermore, as also depicted in FIG. 6, the tolerance is such that lateral movement of the leaflets 14 is limited by the contact between the lateral edge of the ear 32 and the facing surface of the shallow socket section 48.

As soon as normal blood flow through the valve 10 in the direction of the arrow 18 stops, back pressure of the blood from below the valve 10 acts against the two interior facing surfaces 54 of the leaflets 14 causing the closing pivoting movement to begin. At this point, the pivot axis of the leaflets is defined by the bottom of the ears 32 which are supported at the base 50 of the socket. At the same time, the knobs 34 are sliding freely in the slots 46. However, the angular orientation of the slots 46 is such that, when the leaflets have pivoted to a position about halfway between open and closed, full contact between the underside of the knob 34 and the lower surface of the slot 46 begins, causing the bottom of the ear 32 to move upward away from the base 50. Accordingly, the pivot axis of the leaflet moves relative to the centerline of the valve passageway 16, i.e., away from the base 50, as the bottom or underside of the ear 32 is pulled up the inward wall of the shallow socket section 48.

As a result of the angular orientation of the slot 46, when the leaflets 14 reach the fully closed position, as shown in FIG. 5, the bottom of the ear 32 is spaced a short distance from the base 50. Accordingly, the combination of the knob 34 plus the slots 46 prevents wear of pivoting motion from being concentrated at the base 50 for 100 percent of the time, and it also eases the tolerance requirements for achieving a very close fit simultaneously between the straight edge surfaces 42 of the leaflets and between the elliptical edge surfaces 44 and the interior wall surface 28 of the annular valve body.

As soon as the pumping stroke of the respective ventricle begins, the pressure of blood on the upper surfaces 56 of the leaflets 14 causes pivoting motion in the opposite direction to begin because the major surface area portions lie generally radially outward of the eccentric axes defined by the lower ends of the ears 32. The knobs 34 moving in the slots 46 again guide the pivoting motion and gradually lower the ears 32 until contact is again made with the base 50. Pivoting continues until the leaflets 14 reach the position as shown in FIG. 3 where they are preferably disposed at an angle of between about 5° and about 10° to the vertical or centerline of the passageway. Thus, the pivoting movement of each leaflet 14 is preferably between about 45° and about 70°.

Although the invention has been described with regard to a particular preferred embodiment that constitutes the best mode presently known to the inventor, it should be understood that various changes and modifications as would be obvious to one having the ordinary skill in this art may be made without departing from the scope of the invention which is defined solely by the appended claims. For example, should it be desired to achieve a better seal along the arcuate edge surfaces 44 of the leaflets in the closed position, inwardly protruding ledges can be provided in the central passageway, as described and illustrated in the above-mentioned patent application.

Various features of the invention are emphasized in the claims which follow.

What is claimed is:
1. A heart valve prosthesis comprising
an annular valve body having a central passageway therethrough,
a pair of leaflets which are proportioned to jointly close said passageway, and
means mounting said leaflets for substantially pivotal movement between a closed position blocking blood flow through said central passageway and an open position allowing blood flow therethrough,
said mounting means including projections extending in opposite directions from the lateral sides of each of said leaflets and generally diametrically opposed slots in said annular valve body wherein each of said projections is respectively disposed, each of said slots extending along a substantially straight line displaced from a plane perpendicular to the centerline of said passageway by an angle of between about 20° and about 40° in a direction outward from the center and upstream of blood flow,
said projections having rounded ends and said slots being open at the outward end thereof and curved at the other end with a radius of curvature proportioned to the curvature of said rounded ends, whereby said slots guide the pivotal movement of said leaflets by defining the path along with said projections can travel during opening and closing movement.

2. A heart valve comprising
an annular valve body having a central passageway therethrough,
a pair of leaflets which are proportioned to jointly close said passageway, and means mounting said leaflets for substantially pivotal movement between a closed position blocking blood flow through said central passageway and an open position allowing blood flow therethrough, said mounting means including projections extending in opposite directions from the lateral sides of each of said leaflets and generally diametrically opposed slot means in said annular valve body wherein each of said projections is respectively disposed, said leaflets each including a pair of shoulders at said opposite lateral sides, which shoulders are offset from the portions of said projections received in said slot means, and said shoulders being received in socket means formed in said valve body to define an eccentric pivot axis for each of said leaflets whereby said slot means guides the pivotal movement of said leaflets by defining the path along which said projections can travel during opening and closing movement.

3. A heart valve in accordance with claim 2 wherein said socket means each includes a supporting surface which is transverse to the centerline of said central passageway and which is proportioned to provide a base upon which said shoulder may pivot.

4. A heart valve in accordance with claim 3 wherein said slot means is located relative to said base so that the pivot axis of each of said leaflets moves relative to the centerline through said passageway.

5. A heart valve in accordance with claim 4 wherein said shoulders each moves away from said base when said leaflets swing from the open position to the closed position.

6. A heart valve in accordance with claim 2 wherein said socket means and said slot means are formed in a pair of standard sections which extend upward from the main portion of said annular valve body.

* * * * *